United States Patent [19]
Naglieri et al.

[11] 4,134,912
[45] Jan. 16, 1979

[54] PROCESS FOR PREPARING CARBOXYLIC ACIDS

[75] Inventors: Anthony N. Naglieri, Pine Brook; Nabil Rizkalla, River Vale, both of N.J.

[73] Assignee: Halcon International, Inc., New York, N.Y.

[21] Appl. No.: 740,145

[22] Filed: Nov. 8, 1976

[51] Int. Cl.$^2$ .................. C07C 51/12; C07C 51/14
[52] U.S. Cl. .................. 562/579; 260/413; 560/105; 560/106; 560/114; 560/232; 562/406; 562/497; 568/671; 568/659; 568/635
[58] Field of Search ............ 260/532, 413, 476 R, 260/488 K, 515 R, 514 M; 560/232, 105, 106, 114

[56] References Cited

U.S. PATENT DOCUMENTS

| | | | |
|---|---|---|---|
| 3,717,670 | 2/1973 | Schultz | 260/488 K |
| 3,769,324 | 10/1973 | Paulik et al. | 260/488 K |
| 3,769,329 | 10/1973 | Paulik et al. | 260/488 K |

*Primary Examiner*—Vivian Garner
*Attorney, Agent, or Firm*—William C. Long; David Dick; Riggs T. Stewart

[57] ABSTRACT

A carboxylic acid, such as acetic acid, is prepared from a hydrocarbyl alcohol, such as methanol, in carbonylation processes comprising the use of an iodide, carbon monoxide and a nickel catalyst in the presence of a tin promoter.

4 Claims, No Drawings

PROCESS FOR PREPARING CARBOXYLIC ACIDS

This invention relates to the preparation of carboxylic acids, more particularly mono-carboxylic acids, and especially lower alkanoic acids, such as acetic acid, by carbonylation.

Acetic acid has been known as an industrial chemical for many years and large amounts are used in the manufacture of various products. Proposals for producing carboxylic acids by the action of carbon monoxide upon alcohols (carbonylation) have been described, for example in Reppe et al U.S. Pat. No. 2,729,651. However, such prior proposals involving carbonylation reactions have required the use of very high pressures. More recently, carbonylation at lower pressures has been proposed. French Pat. No. 1,573,130, for example, describes the carbonylation of methanol and mixtures of methanol with methyl acetate in the presence of compounds of Group VIII noble metals such as iridium, platinum, palladium, osmium and ruthenium and in the presence of bromine or iodine under more moderate pressures than those contemplated by Reppe et al. Similarly, South African Pat. No. 68/2174 produces acetic acid from the same reactants using a rhodium component with bromine or iodine. Schultz (U.S. Pat. Nos. 3,689,533 and 3,717,670) has disclosed a vapor-phase process for acetic acid production employing various catalysts comprising a rhodium component dispersed on a carrier. These later carbonylation disclosures, however, require the use of expensive noble metals. It is an object of the present invention to provide an improved process for the manufacture of carboxylic acids, especially lower alkanoic acids, such as acetic acid, which requires neither high pressures nor Group VIII noble metals.

In accordance with the invention, it has been surprisingly discovered that a hydrocarbyl alcohol can be carbonylated at relatively low pressures if the carbonylation is carried out in the presence of a nickel catalyst, in the presence of a tin promoter and in the presence of an iodide in an amount which is substantially greater than disclosed by Reppe et al, i.e., at least 10 mols of an iodide, calculated as I, per 100 mols of the alcohol. The surprising discovery has been made that this catalyst-promoter system when used with the indicated high iodide concentration makes possible carbonylation at relatively low pressures, especially carbon monoxide partial pressures, in contrast to the process disclosed in Reppe et al 2,729,651 in which, while employing a nickel-containing catalyst, the patentees find it necessary to use pressures of at least 200 atmospheres in their examples.

Thus, in accordance with the invention, carbon monoxide is reacted with a hydrocarbyl alcohol such as a lower alkyl alcohol, to produce a carboxylic acid, such as a lower alkanoic acid, the carbonylation taking place in the presence of an iodide, e.g., a hydrocarbyl iodide, especially a lower alkyl iodide, such as methyl iodide in an amount of the order specified above. Thus, acetic acid, for example, can be effectively prepared in a representative case by subjecting methyl alcohol to carbonylation in the presence of at least 10 mols methyl iodide per 100 mols of methanol, the carbonylation being carried out in the presence of the catalyst promoter-system described above.

It will be understood that the iodine moiety does not have to be added to the system as a hydrocarbyl iodide but may be supplied as another organic iodide or as the hydroiodide or other inorganic iodide, e.g., a salt, such as the alkali metal or other metal salt, or even as elemental iodine. Following the reaction the organic components of the reaction mixture are readily separated from one another, as by fractional distillation.

In like manner, other lower alkanoic acids, such as propionic acid, butyric acid, and valeric acid, can be produced by carbonylating the corresponding lower alkyl alcohol such as ethyl alcohol, propyl alcohol, and the like. Similarly, other alkanoic acids, such as those containing up to 12 carbon atoms, for example capric acid, caprylic acid, and lauric acid, and like higher carboxylic acids are produced by carbonylating the corresponding alcohol, e.g., alkyl alcohols containing up to 11 carbon atoms in the alkyl group, heptyl alcohol, nonyl alcohol, undecyl alcohol, phenol, and the like.

The above-described reactions can be expressed as follows:

$$CO + ROH \rightarrow RCOOH \quad (1)$$

wherein R is a hydrocarbyl radical which may be saturated, e.g., alkyl of 1 to 11 carbon atoms, or monocyclic aryl, e.g., phenyl or aralkyl, e.g., benzyl. Preferably, R is lower alkyl, i.e., an alkyl group of 1 to 4 carbon atoms, such as methyl, ethyl, n-propyl, i-propyl, n-butyl, sec-butyl, and t-butyl.

The hydrocarbyl radical may be substituted with substituents which are inert in the reactions of the invention.

The more volatile components such as alkyl iodide and unreacted alcohol and byproducts such as esters and ethers in the final product mixture can be readily removed, as by distillation, for recycling, and the net yield of product is substantially exclusively the desired carboxylic acid. In the case of liquid-phase reaction which is preferred, the organic compounds are easily separated from the metal-containing components, as by distillation. The reaction is suitably carried out in a reaction zone to which the carbon monoxide, the alcohol, the iodide and the nickel catalyst and the promoter are fed.

In carrying out the process of the invention, a wide range of temperatures, e.g., 25 to 350° C are suitable but temperatures of 100 to 250° C are preferably employed and the more preferred temperatures generally lie in the range of 125 to 225° C. Temperatures lower than those mentioned can be used but they tend to lead to reduced reaction rates, and higher temperatures may also be employed but there is no particular advantage in their use. The time of reaction is also not a parameter of the process and depends largely upon the temperature employed, but typical residence times, by way of example, will generally fall in the range of 0.1 to 20 hours. The reaction is carried out under super-atmospheric pressure but, as previously mentioned, it is a feature of the invention that excessively high pressures, which require special high-pressure equipment, are not necessary. In general, the reaction is effectively carried out by employing a carbon monoxide partial pressure which is preferably 15 to 1000 psi and most preferably 30 to 200 psi, although carbon monoxide partial pressures of 1 to 10,000 psi can also be employed. By establishing the partial pressure of carbon monoxide at the values specified, adequate amounts of this reactant are always present. The total pressure is, of course, that which will provide the desired carbon monoxide partial pressure and preferably it is that required to maintain the liquid phase and in this case the reaction can be advantageously carried out in an autoclave or similar apparatus. The final reaction mixture will normally contain volatile components such as hydrocarbyl iodide, unreacted alcohol and may contain the corresponding ester and/or ether along with the product acid and these volatile components, after separation from the acid, can be recycled to the reaction. At the end of the desired residence time the reaction mixture is separated into its several constituents, as by distillation. Preferably, the reaction product is introduced into a distillation zone which may be a fractional distillation column, or a series of columns, effective to separate the volatile components from the product acid and to separate the product acid from the less volatile catalyst and promoter components of the reaction mixture. The boiling points of the volatile components are sufficiently far apart that their separation by conventional distillation presents no particular problem. Likewise, the higher-boiling organic components can be readily distilled away from the metal catalyst components and any tin promoter which may be in the form of a relatively non-volatile compound. Nickel catalyst, as well as promoter, including the iodide component, can then be combined with fresh amounts of alcohol and carbon monoxide and reacted to produce additional quantities of acid.

The ratio of the iodide to the alcohol in the reaction system can vary over a wide range as long as it is at least 10 mols per hundred mols of alcohol but ordinarily more than 200 mols of iodide, expressed as I, per 100 mols of alcohol are not used. Typically, there are used 10 to 50 mols of the iodide per 100 mols of alcohol, preferably 17 to 35 mols per 100 mols.

The process is advantageously carried out in the presence of a solvent or diluent, particularly when the reactant has a relatively low boiling point, as in the case of methanol. The presence of a higher-boiling solvent or diluent, which may be the product acid itself, e.g., acetic acid in the case of methanol, or which may be the corresponding ester, e.g., methyl acetate, again in the case of methanol, will make it possible to employ more moderate total pressure. Alternatively, the solvent or diluent may be any organic solvent which is inert in the environment of the process such as hydrocarbons, e.g., octane, benzene, toluene, and the like. The carboxylic acid, when used, should preferably correspond to the acid being produced. A solvent or diluent other than the product itself is suitably selected which has a boiling point sufficiently different from the desired product in the reaction mixture so that it can be readily separated, as will be apparent to persons skilled in the art.

The carbon monoxide is preferably employed in substantially pure form, as available commercially, but inert diluents such as carbon dioxide, nitrogen, methane, and noble gases can be present if desired. The presence of inert diluents does not affect the carbonylation reaction but their presence makes it necessary to increase the total pressure in order to maintain the desired CO partial pressure. The presence of minor amounts of water such as may be found in the commercial forms of the reactants is, however, entirely acceptable. Hydrogen which may be present as an impurity is not objectionable and even may tend to stabilize the catalyst. Indeed, in order to obtain low CO partial pressures the CO fed may be diluted with hydrogen or any inert gas such as those above mentioned. It has been surprisingly found that the presence of hydroen does not lead to the formation of reduction products. The diluent gas, e.g., hydrogen, may generally be used in an amount up to about 95% if desired.

The nickel catalyst component can be employed in any convenient form, viz., in the zero valent state or in any higher valent form. For example, the nickel to be added may be the metal itself in finely divided form, or a compound, both organic or inorganic, which is effective to introduce the nickel into the reaction system. Thus, typical compounds include the carbonate, oxide, hydroxide, bromide, iodide, chloride, oxyhalide, hydride, lower alkoxide (methoxide), phenoxide or nickel carboxylates wherein the carboxylate ion is derived from an alkanoic acid of 1 to 20 carbon atoms such as acetates, butyrates, decanoates, laurates, benzoates, and the like. Similarly, complexes of nickel can be employed, for example, nickel carbonyls and metal alkyls as well as chelates, association compounds and enol salts. Examples of other complexes include bis-(triphenyl phosphine) nickel dicarbonyl, tricylopentadienyl trinickel dicarbonyl, and tetrakis (triphenyl phosphite) nickel.

Particularly preferred are the elemental form, compounds which are iodides, and organic salts, e.g., salts of the monocarboxylic acid corresponding to the acid being produced. It will be understood that the foregoing compounds and complexes are merely illustrative of suitable forms of the nickel catalyst and are not intended to be limiting.

The nickel catalyst component employed may contain impurities normally associated with the commercially available metal or metal compounds and need not be purified any further.

The tin promoter may also have any of the forms mentioned above in connection with the nickel catalyst component but preferably the tin is employed in elemental form or in the form of a halide, such as stannic iodide, stannous iodide, stannic chloride and stannic bromide, or a hydrocarbyl tin compound such as tetraphenyl tin, tetra n-butyl tin and dibutyl diphenyl tin, or an oxide such as stannous oxide and stannic oxide, or an organo oxide such as dimethyl tin oxide and diphenyl tin oxide, or a carboxylate such as stannous caproate and tri n-propyltin acatate, or an organo-halide such as dimethyl tin di-chloride and methyl tin trichloride. The most preferred tin compounds are the halides, the organo halides and the hydrocarbyl tins.

The amount of nickel is in no way critical and is not a parameter of the process of the invention and can vary over a wide range. As is well known to persons skilled in the art, the amount of catalyst used is that which will provide the desired suitable and reasonable reaction rate since reaction rate is influenced by the amount of catalyst. However, essentially, any amount of catalyst will facilitate the basic reaction and can be considered a catalytically-effective quantity. Typically, however, the nickel component of the catalyst is employed in the amount of 1 mol per 5 to 10,000 mols of alcohol, preferably 1 mol per 10 to 5,000 mols of alcohol, and most preferably 1 mol per 30 to 1000 mols of alcohol.

The quantity of tin promoter can also vary widely but typically it is used in the amount of 1 mol per 1 to 10,000 mols of alcohol, preferably 1 mol per 10 to 5000, most preferably 1 mol per 30 to 1000 mols of alcohol.

In the working up of the reaction mixtures, e.g., by distillation, as discussed above, the nickel and the tin generally remain as the least volatile components, and are suitably recycled. The nickel may, however, distill with the volatile components, e.g., in the case of nickel carbonyl. The same is true of the tin component.

It will be apparent that the above-described reactions lend themselves readily to continuous operation in which the reactants and catalyst, preferably in combination with the promoter, are continuously supplied to the appropriate reaction zone and the reaction mixture continuously distilled to separate the volatile organic constituents and to provide the desired product or products, e.g., carboxylic acid, with the other organic components being recycled and, in the case of liquid-phase reaction, a residual nickel-containing (and promoter-containing) fraction also being recycled. It has been observed that hydrogen, e.g., used as a CO diluent as indicated above, is of value in maintaining the catalyst at maximum activity on repeated recycle. During continuous operation, it will be apparent that the iodine moiety remains in the system at all times subject only to occasional handling losses or purges. The small amount of iodine makeup which may be needed from time to time is preferably effected by supplying the iodine in the form of the hydrocarbyl iodide but, as pointed out above, the iodine moiety may also be supplied as another organic iodide or as the hydrogen iodide or other inorganic iodide, e.g., a salt, such as the alkali metal or other metal salts, or as elemental iodine.

The following examples will serve to provide a fuller understanding of the invention, but it is to be understood that they are given for illustrative purposes only, and are not to be construed as limitative of the invention. In the examples, all parts are on a molar basis and all percentages are by weight, unless otherwise indicated. The various reactants and catalyst components are charged to the reaction vessel which is then closed and brought to the reaction temperature indicated.

EXAMPLE I

Methanol (100 parts), tetraphenyl tin (4.6 parts), nickel diacetate tetrahydrate (2 parts) and methyl iodide (32 parts) are charged at room temperature into a pressure vessel which is pressured to 400 psig with carbon monoxide. The vessel is stirred for 14 hours at 150° C. Analysis of the reaction effluent by gas chromatography shows it to contain 37.4 mol % dimethyl ether, 10.9 mol % methanol, 43 mol % methyl acetate and 8.7 mol % acetic acid.

EXAMPLE 2

Methanol (100 parts) tetraphenyl tin (4.6 parts), nickels diacetate tetrahydrate (2parts), and methyl iodide (32 parts) are charged at room temperature into a pressure vessel which is pressure to 350 p.s.i.g. with carbon monoxide and then pressured to 500 p.s.i.g. with hydrogen. The vessel is stirred for 12 hours at 150° C. G. C. analysis of the reaction effluent shows it to contain 32 mol % dimethyl ether, 10 mol % methanol, 46 mol % methylacetate and 12 mol % acetic acid.

EXAMPLE 3

Methanol (100 parts), tin diioxide (4.6 parts), nickel acetate (2 parts), and methyl iodide (32 parts) are charged at room temperature into a pressure vessel which is pressured to 350 p.s.i.g. with carbon monoxide and then pressured to 500 p.s.i.g. with hydrogen. The vessel is stirred for 12 hours at 150° C. G. C. analysis of the reaction effluent shows it to contain 30 mol % dimethyl ether, 9 mol % methanol, 48 mol % methyl acetate and 13 mol % acetic acid.

What is claimed is:

1. A process for the preparation of a monocarboxylic acid which comprises reacting carbon monoxide and a hydrocarbyl alcohol in the presence of an iodide and in the presence of a catalyst consisting essentially of nickel or a nickel compound and a promoter which is tin or a tin compound, said iodide being employed in the amount of at least 10 mols, expressed as I, per 100 mols of alcohol, said reacting being carried out at a temperature of 25–350° C and at a carbon monoxide partial pressure of 1–10,000 psi.

2. A process as defined in claim 1, wherein the acid is a lower alkanoic acid, and the hydrocarbyl alcohol is a lower alkyl alcohol.

3. A process as defined in claim 1, wherein the acid is acetic acid and the hydrocarbyl alcohol is methanol.

4. A process as defined in claim 1, wherein the reaction is carried out under a carbon monoxide partial pressure of 15 to 1,000 psi.

* * * * *